United States Patent [19]

Hooven

[11] Patent Number: 4,676,772
[45] Date of Patent: Jun. 30, 1987

[54] ADJUSTABLE IMPLANTABLE VALVE HAVING NON-INVASIVE POSITION INDICATOR

[75] Inventor: Michael D. Hooven, Miami, Fla.

[73] Assignee: Cordis Corporation, Miami, Fla.

[21] Appl. No.: 812,782

[22] Filed: Dec. 23, 1985

[51] Int. Cl.4 .......................................... A61M 27/00
[52] U.S. Cl. .......................................... 604/9; 116/204
[58] Field of Search .............. 116/204, 277, 284, 298, 116/309–311; 128/1 R, 748; 604/9–10

[56] References Cited

U.S. PATENT DOCUMENTS

| 28,722 | 6/1960 | Whitacker | 137/508 |
|---|---|---|---|
| 79,436 | 6/1868 | Bechtel | 137/508 |
| 1,139,455 | 5/1915 | Gase | 137/508 |
| 1,159,214 | 11/1915 | Gueux | 137/508 |
| 1,199,152 | 9/1916 | Bruce | 137/508 |
| 1,468,434 | 9/1923 | Zander . | |
| 2,207,382 | 7/1940 | McNamara | 277/21 |
| 2,290,151 | 7/1942 | McCollum | 237/12.3 |
| 2,637,618 | 5/1953 | Ray | 116/204 X |
| 2,836,144 | 5/1958 | Morphis | 116/204 |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 128/350 |
| 3,308,798 | 3/1967 | Snider | 123/119 |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,683,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,777,737 | 12/1973 | Bucalo | 128/1 R |
| 3,782,410 | 1/1974 | Steuby | 137/496 |
| 3,804,113 | 4/1974 | Garcea | 137/496 |
| 3,817,237 | 6/1974 | Bolduc | 128/1 R |
| 3,827,439 | 8/1974 | Schulte et al. | 128/350 |
| 3,886,948 | 6/1975 | Hakim et al. | 128/350 V |
| 3,889,687 | 6/1975 | Harris | 128/350 V |
| 3,901,245 | 8/1975 | Spitz et al. | 128/350 V |
| 3,924,635 | 12/1975 | Hakim | 128/350 V |
| 3,970,105 | 7/1976 | Pelton et al. | 137/498 |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,016,827 | 4/1977 | Lawrence | 116/204 |
| 4,103,689 | 8/1978 | Leighton | 128/350 V |
| 4,106,510 | 8/1978 | Hakim et al. | 128/350 V |
| 4,156,422 | 5/1979 | Hildebrandt et al. | 128/748 |
| 4,167,952 | 9/1979 | Reiniecke | 137/493 |
| 4,215,695 | 8/1980 | Spitz et al. | 128/350 |
| 4,246,930 | 1/1981 | Bishop | 137/493.9 |
| 4,332,255 | 6/1982 | Hakim et al. | 128/350 |
| 4,340,038 | 7/1982 | McKean | 128/1.3 |
| 4,360,007 | 11/1982 | Levy et al. | 128/1 R |
| 4,437,493 | 3/1984 | Okuda et al. | 138/45 |
| 4,443,214 | 4/1984 | Marion | 604/9 |
| 4,452,423 | 6/1984 | Bevlavi | 251/65 |
| 4,540,400 | 9/1985 | Hooven | 604/9 |
| 4,541,429 | 9/1985 | Prosl et al. | 128/1 R |
| 4,551,128 | 11/1985 | Hakim et al. | 604/9 |

FOREIGN PATENT DOCUMENTS 68509 of 0000 Netherlands .

Primary Examiner—Dalton L. Truluck
Attorney, Agent, or Firm—Lockwood, Alex, FitzGibbon & Cummings

[57] ABSTRACT

A non-invasively adjustable cerebrospinal fluid pressure relief valve includes a magnetized element which is positionable, through application of an external magnetic field, to permit post-implantation adjustment of the valve's opening threshold pressure setting. An indicator for non-invasively ascertaining the relative adjustment setting of the valve following implantation includes a magnetic pointer which rotates to a position in alignment with the magnetic field produced by the magnetized element. To provide a reference against which the relative valve setting can be measured, the indicator includes an alignment structure which repeatably orients the indicator relative to the implanted valve.

19 Claims, 7 Drawing Figures

ADJUSTABLE IMPLANTABLE VALVE HAVING NON-INVASIVE POSITION INDICATOR

BACKGROUND OF THE INVENTION

The present invention relates to intracranial pressure relief valves and, more particularly, to a position sensor for non-invasively sensing the position of a magnetic wrench in a non-invasively adjustable intracranial pressure relief valve.

Hydrocephalus is a condition in which the body, for any one of a variety of reasons, is unable to relieve itself of excess cerebrospinal fluid (CSF). The collection of excess CSF in the ventricular spaces of the brain results in an increase of both epidural and intradural pressures which, in turn, causes a number of adverse physiological effects, including compression of brain tissue, impairment of blood flow in the brain tissue and impairment of the brain's normal metabolism.

Treatment of a hydrocephallic condition frequently involves relieving the accompanying abnormally high intracranial pressure. A variety of CSF pressure regulator valves and methods for controlling CSF pressure have been developed which include various forms of check valves, servo valves or combinations thereof. Generally, such valves serve to divert CSF from the ventricles of the brain through a discharge line to some suitable drainage area of the body such as the veinous system or the peritineal cavity. Both check valves and servo valves operate to avoid the development of abnormally high intracranial pressures, and preferably serve to maintain such pressures within limits which vary according to the specific requirements of individual patients. Accordingly, CSF pressure relief valves frequently include various forms of mechanisms which permit the pressure-flow characteristics of the valve to be adjusted as necessary to suit the needs of particular patients.

In one CSF relief valve, as disclosed in co-pending application Ser. No. 467,326, filed Feb. 17, 1983 by the present inventor, a diaphragm containing a valve seat is positioned in a valve casing, and both sides of the diaphragm are exposed to the CSF fluid. A ball-shaped valve closure member is mounted to a threaded screw member in the casing so as to engage the valve seat. The force by which the closure member engages the valve seat, and thus the pressure differential at which the valve permits CSF fluid flow, can be adjusted by threading the screw member in or out prior to implantation of the valve within a patient.

It frequently develops however, that optimum performance of the valve may be obtained at an adjustment setting other than that to which the valve was set at the time of implantation. Once implanted, readjustment of the valve would require invasive surgery and hence would be justified only in the case of gross misadjustment.

To permit simple readjustment of implanted CSF pressure relief valves, non-invasively adjustable valves have been developed. Once such valve is that disclosed in co-pending application of the present inventor Ser. No. 515,700, filed July 21, 1983, in which a rotatable magnetic element or wrench is coupled to a threaded screw member within the valve. By bringing a specially constructed magnetic tool into the vicinity of the implanted valve, magnetic communication is established between the tool and the magnetic wrench to permit a physician to rotate the wrench and thereby alter the pressure-flow characteristics of the implanted valve. Since magnetic coupling between the tool and the wrench is employed, a completely non-invasively adjustable valve is provided.

To permit a physician to determine the relative adjustment setting of such an implanted, magnetically adjustable valve, it is necessary that a complete and accurate record of the initial valve setting, together with any subsequent readjustments thereof, be maintained. This places an increased burden on health care personnel and creates the risk that accurate knowledge of the valve adjustment setting might be inadvertently lost.

The present invention concerns a CSF valve system wherein a non-invasive position sensor and indicator are provided for indicating the relative adjustment setting of the implanted valve. The valve position sensor includes a pivotally mounted magnetic indicator member which can be placed in the vicinity of an implanted valve. The magnetic field produced by the magnetic wrench causes the pivotable magnetic member to rotate to a position aligned with the magnetic field lines. An indexing mechanism assures that the position sensor is located in the same position relative to the valve during each measurement of the magnetic wrench position. Accordingly, the position of the magnetic indicator member will vary in accordance with the setting of the implanted valve. This permits health care personnel to quickly, accurately and non-invasively ascertain the relative adjustment setting of the implanted valve whenever necessary.

Accordingly, it is an object of the present invention to provide a magnetically adjustable CSF pressure relief valve system having an indicator for indicating the relative adjustment setting of the implanted valve.

It is a more specific object of the present invention to provide a position sensor for non-invasively indicating the relative adjustment setting of a magnetically adjustable CSF pressure relief valve.

SUMMARY OF THE INVENTION

An adjustment setting indicator is provided for indicating the relative setting of an implanted adjustable valve of the type in which a relatively rotatable magnetic member is rotated, by means of an externally applied magnetic field, to adjust the relative setting of the valve. The indicator includes a relatively non-rotatable reference member together with an indexing arrangement for orienting the reference member relative to the implanted valve when the indicator is positioned adjacent the valve. When so positioned, the reference member establishes a unique line of reference relative to the implanted valve. A relatively rotatable magnetic indicator mounted to the reference member indicates the direction of applied magnetic field. When the indicator is positioned adjacent the implanted valve, the pointer indicates the direction of the magnetic field produced by the magnetic member of the valve. The position of the indicator pointer, relative to the line of reference established by the reference member, provides an indication of the valve setting.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
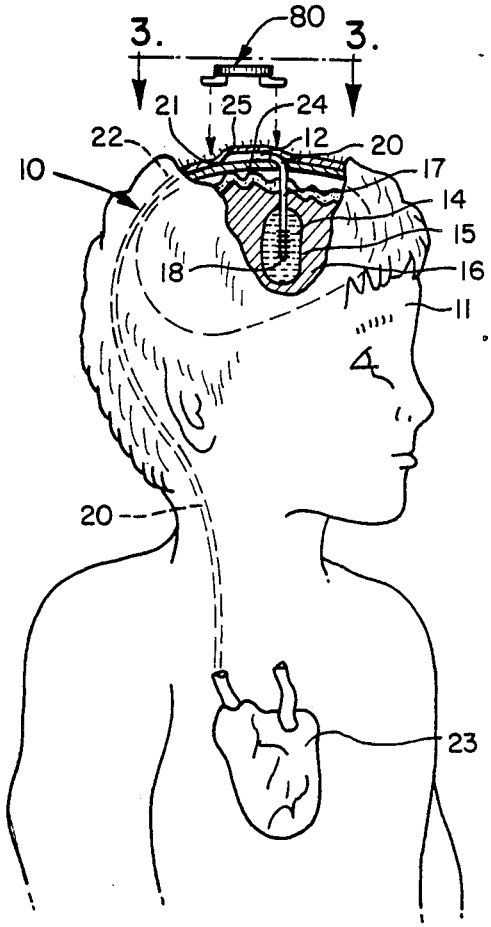
FIG. 1 is a perspective view, partially in section, of an implanted hydrocephalus system incorporating a magnetic, non-invasively adjustable, CSF shunt valve.

Referring to the drawings, and particularly to FIG. 1, a hydrocephalus system 10 for maintaining a desired predetermined intracranial pressure in a patient 11 is illustrated. As shown, the system includes a non-invasively adjustable intracranial pressure relief valve 12 for maintaining the desired intracranial pressure.

Cerebrospinal fluid (CSF) 14 is drained from a ventricle 15 of the brain 16 by means of a ventricular catheter 17. Preferably, catheter 17 is radio-opaque to facilitate its accurate placement within the brain. The distal end 18 of catheter 17 may be provided with a plurality of apertures to permit the passage of CSF therethrough.

Opposite distal end 18, the other end of catheter 17 is coupled to an inlet port 20 of valve 12, to provide fluid communication between the valve and the ventricle. An outlet port 21 of the valve is connected to one end of a drain catheter 22, the opposite end of which discharges into an appropriate drainage location in the patient's body, such as, for example, the heart 23 or peritoneal cavity (not shown). The valve 12, together with the extracranial portions of the ventricular catheter 17 and drain catheter 22, is preferably subcutaneously implanted between the patient's skull 24 and scalp 25.

The internal construction and operation of valve 12 may best be understood by reference to FIGS. 2, 4, 6 and 7. As illustrated, the valve includes a valve casing bottom 26, a flexible diaphragm 27, a valve seat 28 and valve closure ball 29, a valve casing top 30, and a threaded screw member 31. The diaphragm 27, valve seat 28 and closure ball 29 together form flow restricting means for restricting the flow of CSF or other fluid through the valve. The casing bottom 26, casing top 30, screw member 31 and closure cap 33 are each formed of a suitable, durable, biologically compatible material, such as thermoplastic polymers of polyethersulfone or polycarbonates.

Figure 4:
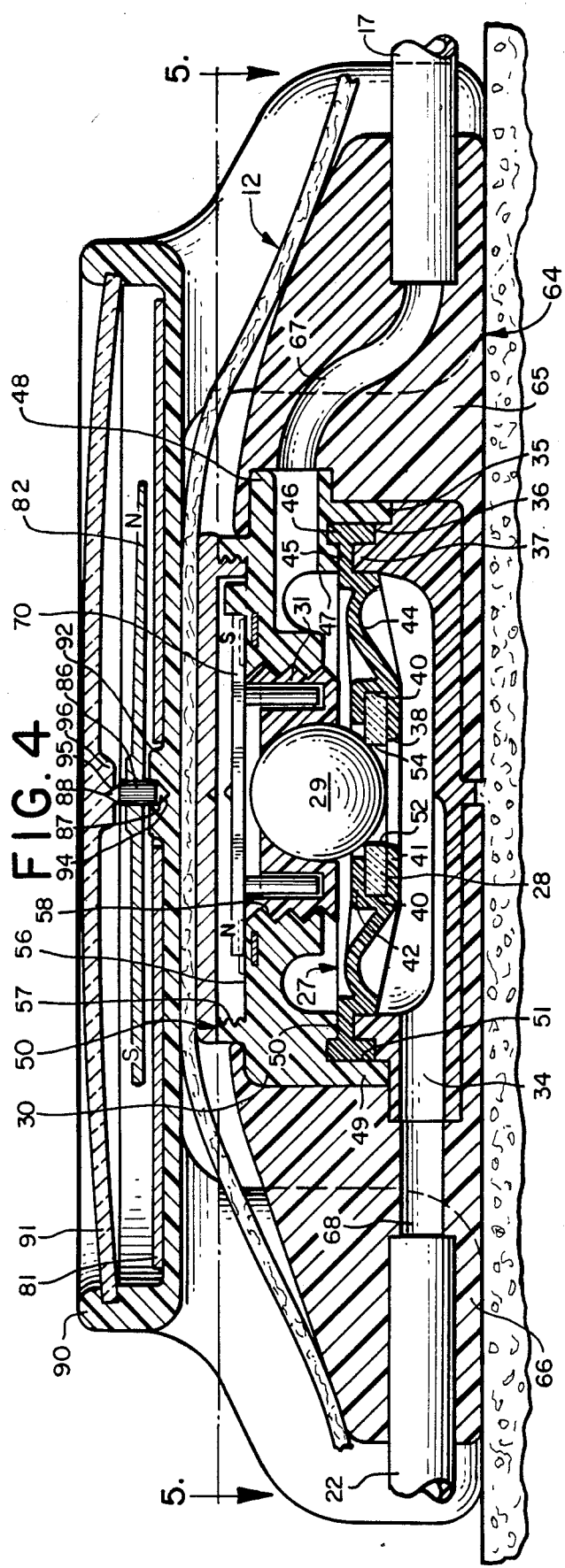
FIG. 4 is a side elevation view of the valve position sensor shown in FIG. 3, showing the sensor in an operating position over an implanted adjustable valve.

The valve casing bottom 26 comprises a substantially cup-shaped member which, as shown in FIG. 4, defines a fluid discharge chamber 34 of preferably elongate cross-section. As illustrated, the upper rim of the casing bottom 26 is provided with a plurality of stepped raised shoulders 35, 36 and 37.

Diaphragm 27 preferably comprises a substantially circular, flexible, movable disc having a fluid flow passage 38 adjacent its center. An annular groove 40, formed in the diaphragm adjacent the flow passage 38, receives and holds the valve seat 28. The groove 40 is defined by a lower flange 41 and an upper flange 42, the upper flange 42 being preferably somewhat shorter than the lower flange 41 in order to accommodate unrestricted movement of the diaphragm and valve seat 28 relative to the valve closure ball 29 during operation of the valve.

The operative surface of the diaphragm 27 comprises an annular disc portion 44 surrounding the lower flange 41. To provide increased flexibility and stability against cocking during operation, the annular disc portion 44 of diaphragm 27 is preferably convoluted as best seen in FIG. 4. A horizontal annular flange 45 surrounds the annular disc portion 44, and in turn is encircled by a generally vertical annular flange 46 to complete the diaphragm construction. In actual practice, the diaphragm 27 may be formed in one piece from any durable, flexible, biologically compatible material, such as silicone rubber.

The valve casing top 30 also comprises a substantially cup-shaped member, which, as shown in FIG. 4, defines an inlet chamber 47 and an inlet port 48, the latter of which is also of elongate oblong cross section. The casing top 30 further includes of pair of downwardly extending annular flanges 49 and 50, with flange 49 being somewhat longer than flange 50. Flanges 49 and 50 are spaced from each other to define a groove 51 therebetween.

The diameter and width of flange 50 are preferably substantially equal to the diameter and width of shoulder 37 on casing bottom 26 to overlie that shoulder when the casing is assembled in the manner shown in FIG. 4. Similarly, the diameter and width of groove 51 are substantially equal to the diameter and width of shoulder 36 of casing bottom 26 to overlie that shoulder when the casing is assembled.

When assembled, the vertical annular flange 46 of diaphragm 27 is clamped between groove 51 and shoulder 36 as illustrated, thereby firmly fixing the position of the diaphragm relative to the casing top and bottom members 30 and 26 respectively. The vertical dimensions of shoulders 35, 36, 37 and flanges 49 and 50 are such that the diaphragm fits snugly between the assembled casing members, which are then bonded together by means of a solvent, adhesive or by ultrasonic welding.

The valve seat 28 preferably comprises a circular disc shaped member having a circular opening 52 (FIG. 4) through its center to permit fluid to pass through the diaphragm. A shoulder 54, formed at the top of the valve seat opening 52, cooperates with the valve closure ball 29 to block passage of fluid through the opening.

The valve closure ball 29 is positioned above the diaphragm and is preferably spherical in shape, although other shapes may be satisfactorily employed. Both the valve seat 28 and the closure ball 29 are formed of a durable, biologically compatible material such as, for example, sapphire.

Figure 2:
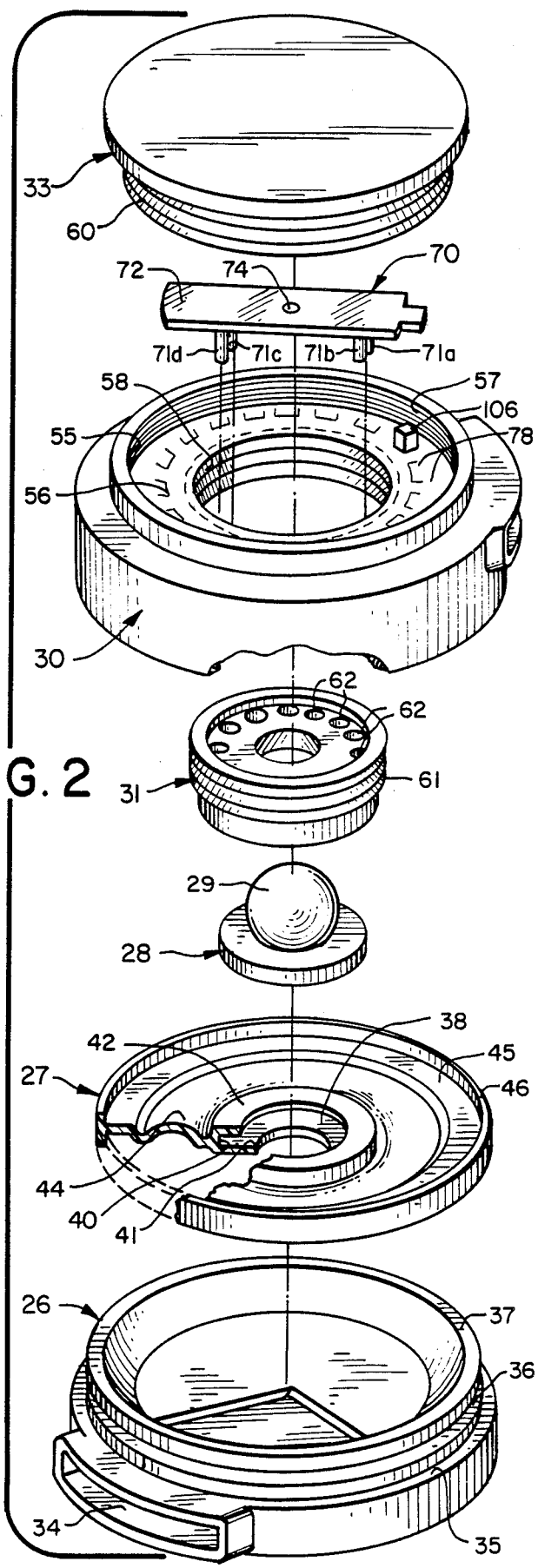
FIG. 2 is an enlarged, exploded view of the non-invasively adjustable valve of FIG. 1 illustrating the principal components thereof.

Referring to FIG. 2, the upper surface of the top valve casing 30 includes an aperture 55 therethrough. Preferably, the aperture includes regions of two different diameters, the larger of which is toward the upper surface of the top cover to form a ledge or step 56 therebetween. Both the larger diameter region and the narrow diameter region of the aperture are provided with internal threads 57 and 58 respectively.

The casing closure cap 33 includes external threads 60 which engage threads 57 to allow the cap to be turned into casing top 30 and thus seal the valve enclosure. Similarly, a set of external threads 61 along the exterior surface of screw member 31 engage threads 58 to allow the screw member to be engagingly or disengagingly turned into the closure top 30.

As illustrated in FIG. 4 valve closure ball 29 is stationarily received within a recess 62 in the screw member 31. As best seen by reference to FIG. 2, a plurality of equally angularly spaced circular recesses 62 are provided along the upper surface of screw member 31 at a constant radial distance from the center of the member.

Once the upper and lower valve casings 26 and 30, the diaphragm 27, the valve seat 28, the ball 29 and the screw member 31 have been assembled together, the assembled valve casing is then slidably received within a flexible outer housing 64 as illustrated in FIG. 4. The flexible outer housing 64 preferably comprises a pair of housing half members 65 and 66. Housing half member 65 includes a tapering inlet antechamber 67 which communicates at its wider end with the inlet port 47, and at the other end with the ventricular catheter 17. Housing member 66 also includes a tapered discharge antechamber 68 which, at its wider end, communicates with the discharge chamber 34 and at the other, narrower, end communicates with the drain catheter 22. The outer housing 64 is formed of a flexible, biologically compatible, material such as silicone rubber.

Assuming no deflection of diaphragm 27, the force with which ball 29 contacts shoulder 54 is determined primarily by the vertical position of the screw member 31 relative to the casing top 30, which in turn, is governed by the degree to which the screw member is threaded into the casing top. By rotating the screw member such that it extends further from the lower interior surface of the casing top 30, the contact force between the ball 29 and valve seat shoulder 54 may be increased. Similarly, rotating the screw member in the opposite direction reduces the contact force. Accordingly, the pressure-flow characteristics of the valve can be altered in response to such rotation of the screw member.

To provide a mechanism for non-invasively adjusting the rotational position of the screw member, the valve includes a magnetic wrench 70 located within the aperture 55 formed in casing top 30. Wrench 70 is generally elongate in form and includes four downwardly projecting cylindrical protrusions 71a 71b, 71c and 71d formed in rectangular formation along the undersurface thereof. The wrench further includes an elongate magnetic portion 72 having North and South poles at opposite ends thereof. The upper surface of the magnet 72 is provided with an upwardly projecting pivot point 74 adjacent its center as illustrated.

Figure 6:
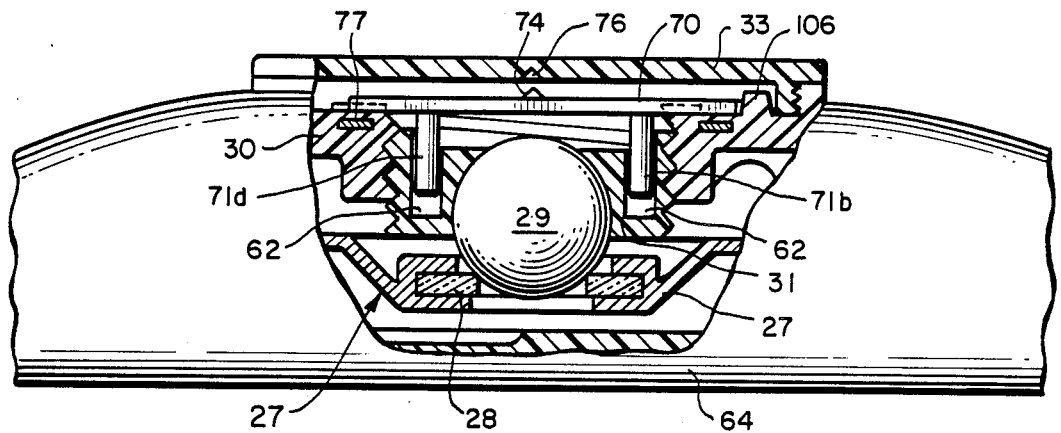
FIG. 6 is a side elevation view, partially in section, showing the non-invasively adjustable valve in its operational mode.
Figure 7:
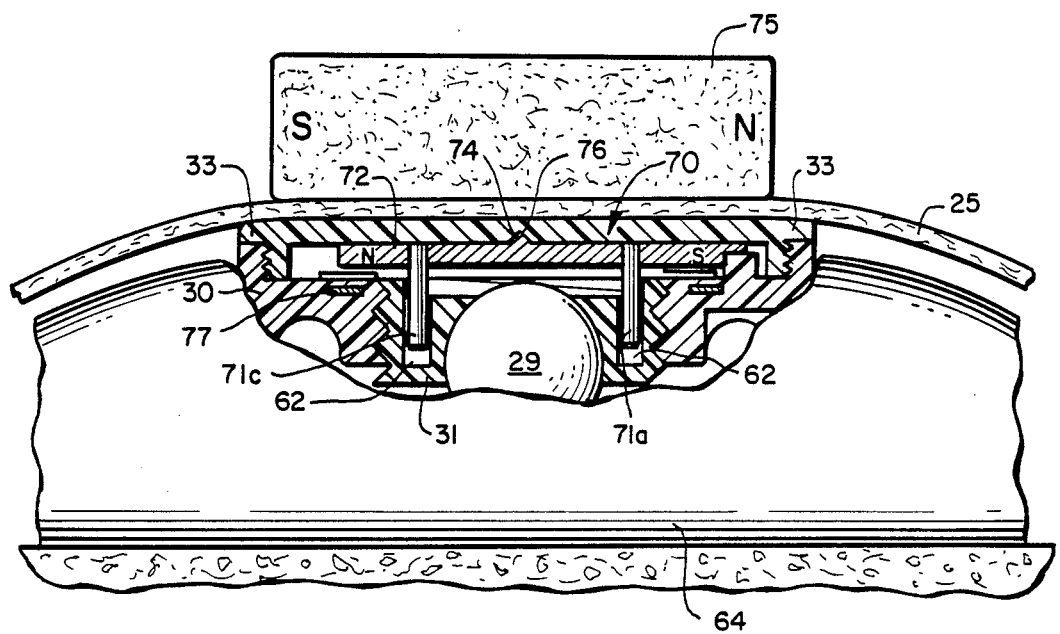
FIG. 7 is a side elevation view, partially in section, showing the non-invasively adjustable valve being adjusted by a valve adjustment tool.

As is best seen in FIGS. 6 and 7, the magnetic wrench 70 is positioned above the screw member 31 such that pins 71a–71d are received within four of the twelve circular recesses 62 in the upper surface of screw member 31. Such engagement of the pins and recesses allows vertical motion of the wrench relative to the screw member, while at the same time assuring that rotation of one results in rotation of the other. Thus, by rotating the magnetic wrench, the vertical position of the screw member, and hence the contact force existing between ball 29 and valve seat shoulder 54, may be continuously adjusted.

To permit adjustment of the valve after its implantation beneath the scalp, a tool containing a bar magnet 75 having north and south poles at opposite ends may be positioned above the scalp directly above the implanted valve as shown in FIG. 7. When the magnet is positioned directly above the magnetic wrench such that the unlike poles of each are adjacent one another, the magnetic wrench will be drawn upwardly so that pivot point 74 is received in a suitably positioned recess 76 formed in the interior surface of casing closure cap 33. Pivot point 74 thus allows the magnetic wrench to rotate relative to the interior surface of cap 33 in response to rotational motion of magnet 75. Such rotation of the wrench results in rotation of the screw member 31 and a corresponding change in the contact force existing between ball 29 and shoulder 54.

To prevent inadvertent or unintentional rotation of the magnetic wrench, the valve includes an annular member 77 formed of a magnetic material embedded in shoulder 56 directly beneath the magnetic wrench 70. In the absence of a strong externally applied magnetic field, the magnetic wrench 70 will be pulled downwardly into contact with step 56 by reason of the attraction between magnet 72 to annular member 77 to the position shown in FIG. 6. As illustrated in FIG. 2, the upper surface of step 56 is provided with a plurality of serrations 78 which serve to increase the friction between the lower surface of the wrench and the casing top 30 to prevent inadvertent rotation of the magnetic wrench when in this position.

Figure 3:
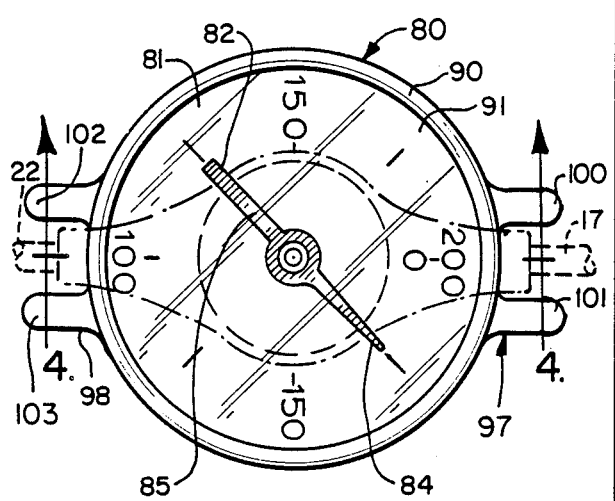
FIG. 3 is an enlarged top plan view of an adjustable valve position sensor constructed in accordance with the invention.

To allow accurate and non-invasive determination of magnetic wrench position, a position sensor 80, constructed in accordance with the invention, is provided and is illustrated in FIGS. 3 and 4. The position sensor comprises a generally circular disc-shaped indicator plate 81 over which an indicator needle 82 is pivotally mounted. The indicator needle is generally elongate in form and includes a head portion 84 and tail portion 85 which needle is preferably together give the needle the general shape of an arrow as illustrated. Midway along its length, the needle includes a generally cylindrical perpendicularly oriented pivot shaft shaped 86 having pointed ends 87 and 88 as illustrated.

Position indicator 80 includes a housing having a generally cup-shaped lower portion 90 in which the indicator plate 81 and needle 82 are received, and an overlying cover 91 preferably formed of a transparent plastic. An upwardly extending pillar 92 is formed adjacent the center of the indicator housing and includes a socket 94 in which one end 87 of pivot shaft 86 is received. Similarly, the remaining end 88 of the shaft is received in a socket 95 formed in the end of a downwardly depending pillar 96 formed on the undersurface of cover 91. When so mounted, needle 92 is rotatable relative to indicator plate 81 around pivot shaft 86.

Indicator needle 82 comprises a permanent magnet having North magnetic polarity at one end and South magnetic polarity at the other. Because the needle is rotatable relative to the indicator plate, in the presence of a static magnetic field will cause the indicator needle will rotate to a position of alignment with the field. To avoid interference with the indicator needle movement, the indicator plate, together with the remaining elements of the position indicator, are preferably formed from durable plastic or other non-magnetic material. To dampen oscillatory motion of the needle, the enclosure for the needle is preferably filled with a suitable clear liquid.

It will be appreciated that the rotatably mounted indicator needle, being sensitive to the direction of externally applied magnetic fields, may be used to sense the position of magnetic wrench 70 since the permanent magnet 72 thereof generates a static magnetic field having a direction corresponding to that of the wrench. Accordingly, when the position sensor 80 is placed over the valve 12 in the manner shown in FIG. 4, the indicator needle 82 will rotate to a position parallel with the longitudinal axis of magnetic wrench 70.

To obtain meaningful indications of the wrench position, it is necessary to establish a reference against which adjustments to the wrench position can be measured. To this end, the position sensor 80 includes indexing means which take the form of a pair of alignment tongs 97 and 98 affixed to the undersurface of the indicator housing 90. Each tong comprises a pair of vertically disposed downwardly depending tabs 100-101 and 102-103 defining channels therebetween. The tongs are located at points diametrically opposite one another on the indicator housing such that the channels formed between members 100 and 101 and 102 and 103 are colinear. The channels formed between tabs 100-103 are of sufficient width as to receive the subcutaneously implanted catheters 17 and 22 together with the scalp 25 overlying each. Preferably, the edge of each tab is rounded to avoid the possibility of damage to the patient's scalp. In this manner, the alignment tongs 97 and 98 enable the position indicator 80 to be repeatably positioned over the implanted valve 12 and thereby maintain a constant orientation relative thereto. Accordingly, the relative position of the needle will reflect a particular orientation of the magnetic wrench 70 relative to the valve casing 30.

To provide a means by which a quantitative record of the valve adjustment may be maintained, the indicator plate preferably includes a plurality of reference numerals 96 along its periphery as illustrated.

In use, the indicator is placed on the patient's head so that implanted catheters 17 and 22 engage alignment tongs 97 and 98 as illustrated in FIG. 3. The position of the needle 82 is then noted to ascertain the relative adjustment setting of the valve. The position sensor may then be removed from the vicinity of the valve and the valve adjusted by means of a suitable magnet 75 (FIG. 7), whereupon the adjustment of the valve may be confirmed by once again bringing the position sensor to a position over the valve. Thus the position sensor serves a function not only of ascertaining the position of the magnetic wrench, but also of confirming that attempted readjustment of the valve has indeed resulted in rotation of the screw member 31.

Figure 5:
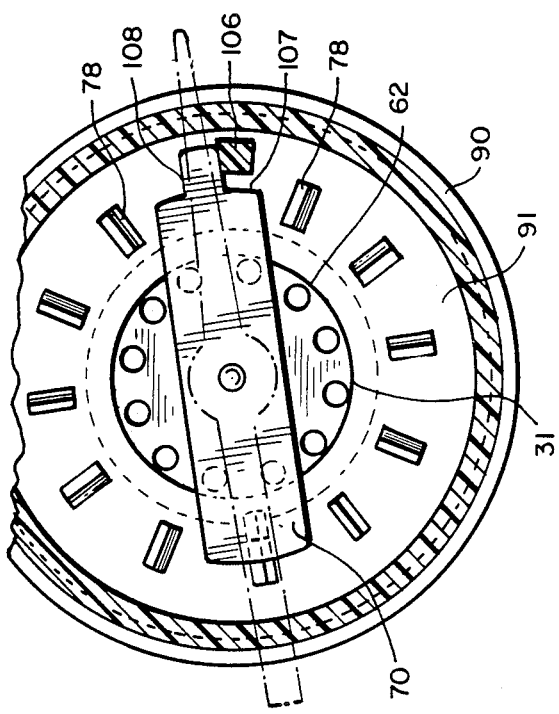
FIG. 5 is an enlarged cross sectional view of the valve shown in FIG. 1, helpful in understanding the operation thereof.

To avoid ambiguity in the indicator needle readings, the valve, in accordance with one aspect of the invention, may be constructed so that the magnetic wrench 70 is confined to no more than 360 degrees rotation. When so constructed, the valve and the position indicator together form a cerebrospinal fluid pressure relief valve system in which the threshold pressure setting of an implanted valve can be unambiguously and non-invasively determined by an external, magnetically coupled indicator. To this end, the valve may include an upwardly projecting stop member 106 on step 56 of the valve casing top 30 as best seen in FIG. 2. The stop member projects into the path of the magnetic wrench 70 to restrict the rotational travel of the wrench. To permit the wrench to rotate through one complete turn, one end of the magnetic wrench may be shortened, as best seen in FIG. 5, to allow that end to swing clear of stop member 106 during rotation. Additionally, a pair of notches 107 and 108 can be formed adjacent the longer end of wrench 70 to further increase the travel of the wrench. Because screw member 31 includes a plurality of holes 62 along the periphery of its upper surface, the screw member may first be adjusted to an approximate or nominal adjustment setting after which the magnetic wrench can be inserted to permit a one turn adjustment of that nominal setting. Accordingly, a wide range of pressure-flow characteristics may be obtained from the valve solely by means of such preadjustment during factory assembly without the need for additional components.

While a specific configuration of the valve position sensor has been shown and described, it will be appreciated by those skilled in the art that numerous modifications may be made without departing from the spirit and scope of the invention. For example, the shape of the indicator needle, the indicator plate, and the sequence of reference numerals shown thereon may be altered as desired. Furthermore, the precise shape and configuration of the alignment tongs may be adjusted to suit particular applications. Finally, the choice of materials for the indicator is not critical provided the materials do not adversely influence movement of the magnetic indicator needle.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A system for controlling the pressure of cerebrospinal fluid, comprising:
    an implantable fluid pressure relief valve having a housing, an adjustment member for setting the opening pressure threshold of said valve, a rotatable magnetic wrench means for adjusting said adjustment member, said relief valve also having means for limiting rotation of said magnetic wrench means to less than 360 degrees when said valve is in an implanted position; and
    magnetic indicator means responsive to the position of said magnetic member for non-invasively indicating the position of said magnetic member to indicate the pressure threshold of said valve.

2. A pressure control system for cerebrospinal fluids as defined in claim 1 wherein said adjustment member is rotatable, and said magnetic wrench means comprises an elongate magnetic wrench mounted for rotation with said adjustment member.

3. A pressure control system for cerebrospinal fluids as defined in claim 1 wherein said magnetic indicator means includes reference means responsive to the orientation of said relief valve housing.

4. A pressure control system for cerebrospinal fluids as defined in claim 2 wherein said indicator means includes a housing and a relatively non-rotatable reference member, said reference member including indexing means on said housing adapted for alignment with said valve housing 5. An indicator for indicating the relative pressure threshold setting of an implanted magnetically adjustable cerebrospinal fluid control valve having a magnetic movable pressure adjustment member, comprising:
 a relatively non-rotatably reference member;
 indexing means on said reference member for orienting said reference member relative to the implanted valve when said reference member is positioned adjacent the valve, said reference member and said indexing means thereby establishing a line of reference relative to the implanted valve; and
 a magnetic indicator rotatably mounted on said reference member for indicating the relative direction of magnetic fields associated with the valve adjustment member.

6. A valve position indicator as defined in claim 5 wherein said magnetic indicator comprises an elongate poitner formed of a magnetic material.

7. A valve position indicator as defined in claim 6 wherein said pointer is magnetized.

8. A valve position indicator as defined in claim 7 wherein the magnetically adjustable valve is subcutaneously implanted and said reference member includes indexing means for orienting said reference member relative to the implanted valve to establish a line of reference relative thereto.

9. A valve position indicator as defined in claim 8 wherein said indexing means comprises a pair of spaced-apart downwardly depending tab portions on said reference member defining a channel therebetween.

10. A valve position indicator for indicating the relative threshold pressure setting of an implanted valve for controlling the passage of body fluids of the type wherein a relatively rotatable magnetic member operatively associated with the valve is rotated by means of an externally applied magnetic field to adjust the relative setting of the valve, said indicator comprising:
 a relatively non-rotatable reference member;
 indexing means on said reference member for orienting said reference member relative to the implanted valve when said reference member is positioned adjacent the valve, said reference member and said indexing means thereby establishing a line of reference relative to the implanted valve; and
 magnetic indicator means rotatably mounted to said reference member for indicating the direction of applied magnetic fields, whereby, said indicator means indicate the direction of the field produced by the magnetic member of the valve to provide an indication of relative valve adjustment setting when said reference member is positioned adjacent the implanted valve.

11. A valve position indicator as defined in claim 10 wherein said reference member is adapted to be placed over a subcutaneously implanted adjustable valve.

12. A valve position indicator as defined in claim 11 wherein said magnetic indicator means comprise an elongate member formed of a magnetic material and having pivotal attachment means along its length.

13. A valve position indicator as defined in claim 12 wherein said reference member comprises a substantially flat member formed of a non-magnetic material, the upper surface of said reference member being provided with a recess defining a housing for receiving said elongate member, said recess being provided with pivotal mounting means for engaging said pivotal attachment means whereby said elongate member is rotably mounted within said housing.

14. A valve position indicator as defined in claim 13 wherein said indexing means are provided on the lower surface of said reference member.

15. A valve position indicator as defined in claim 14 wherein the implanted adjustable valve includes at least one subcutaneously implanted catheter for communicating body fluid to the valve, and said indexing means comprise at least one downwardly depending tab portion defining a channel for receiving said subcutaneously implanted catheter.

16. A valve position indicator as defined in claim 15 wherein said valve includes a pair of subcutaneously implanted catheters, and said indexing means comprise first and second pairs of said tab portions, said first pair receiving one of said pair of subcutaneously implanted catheters and said second pair receiving the other of said subcutaneously implanted catheters.

17. A valve position indicator as defined in claim 10 wherein said magnetic indicator means are magnetized.

18. In an implantable valve for regulating the passage of body fluids from one location in the body to another, said valve having a housing with a fluid chamber therein, an inlet port for admitting fluid from said one location into said chamber, a discharge port for discharging fluid from said chamber to said another location, valve closure means within said chamber to restrict the flow of fluid through said chamber and a rotatable adjustment member for setting the opening pressure threshold of said valve closure means, the improvement comprising:
 limiting means for limiting the rotation of said adjustment member to less than 360 degrees when said valve is in an implanted position.

19. The regulating valve of claim 18 wherein said limiting means comprises a stop member projecting from said housing and a magnetic wrench member which rotates with said adjusting means.

* * * * *